US006113560A

United States Patent [19]

Simnacher

[11] Patent Number: 6,113,560

[45] **Date of Patent: *Sep. 5, 2000**

[54] METHOD AND DEVICE FOR GENERATING SHOCK WAVES FOR MEDICAL THERAPY, PARTICULARLY FOR ELECTRO-HYDRAULIC LITHOTRIPSY

[75] Inventor: Erwin Simnacher, Constance, Germany

[73] Assignee: HMT High Medical Techologies, Lengwil, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/809,246

[22] PCT Filed: Sep. 21, 1994

[86] PCT No.: PCT/EP94/03155

§ 371 Date: May 27, 1997

§ 102(e) Date: May 27, 1997

[87] PCT Pub. No.: WO96/09621

PCT Pub. Date: Mar. 28, 1996

[51] Int. Cl.[7] .......... A61B 17/22

[52] U.S. Cl. .......... 601/4; 367/147

[58] Field of Search .......... 601/4; 604/22; 606/127, 128; 367/147

[56] References Cited

U.S. PATENT DOCUMENTS 3,225,252 12/1965 Schrom et al. .
3,624,324 11/1971 Barkan et al. .
4,821,729 4/1989 Makofski et al. .
4,934,353 6/1990 Nowacki et al. .
4,966,132 10/1990 Nowacki et al. .
5,105,801 4/1992 Cathignol et al. .
5,146,912 9/1992 Eizenhoefer .
5,152,768 10/1992 Bhatta .
5,195,508 3/1993 Muller et al. .
5,231,976 8/1993 Wiksell .
5,245,988 9/1993 Einars et al. .
5,301,659 4/1994 Brisson et al. .
5,380,411 1/1995 Schlief .
5,397,961 3/1995 Ayers et al. .

*Primary Examiner*—Marvin M. Lateef
*Assistant Examiner*—Shawna J Shaw
*Attorney, Agent, or Firm*—R. William Beard, Jr.; Frohwitter

[57] ABSTRACT

The invention concerns a method and device for generating shock waves by spark discharge between electrodes which are intermittently fed with electric current in a fluid medium such as water. The shock waves are focused on the object to be shattered in a body. According to the invention, conductive, semiconductive or polarisable particles (15) are introduced into the fluid medium (14) between the electrodes (3, 4) and retained there owing to the fact that the medium (14) and the particles (15) it contains are accommodated in a casing (11) around the electrodes (3, 4), said casing (11) being permeable to the shock waves. A voltage breakdown in the form of a spark discharge is attained even in cases in which the distance between the electrodes has increased beyond an otherwise critical extent.

16 Claims, 2 Drawing Sheets

METHOD AND DEVICE FOR GENERATING SHOCK WAVES FOR MEDICAL THERAPY, PARTICULARLY FOR ELECTRO-HYDRAULIC LITHOTRIPSY

The invention relates to a method and a device for producing shock waves by spark discharge between electrodes which are supplied with electrical current intermittently in a liquid medium such as water, the shock waves being focussed onto the object located in a body.

A method of this type is disclosed in DE-PS 23 51 247. This document describes a device for fragmentation of concretions in the body of a living being. A spark discharge in a liquid medium is used to produce shock waves at one focus of a truncated rotation ellipsoid, which are reflected on the ellipsoid and are focussed at the second focus. The concretions to be fragmented are positioned at this second focus.

In general, in systems of this type, the spark discharge takes place on a replaceable device in which there are at least two opposite electrodes, between which the discharge takes place.

DE-OS 26 35 635 discloses such a device, substantially comprising two axially arranged electrode tips, a low-induction power supply, and mechanical retention or embedding of the electrodes.

Incorporated in the associated system, the electrodes together with a high-voltage switch and a high-voltage-resistant capacitance form a circuit whose inductance and resistance are very low. During operation, the capacitance is charged to a voltage in the order of magnitude of about 10 kV to 30 kV. This voltage is applied intermittently, via the high-voltage switch, to the electrodes, which are located in an aqueous environment. If the distance between the two electrodes is not too great at the given voltage, then an electrical breakdown in the form of a spark discharge takes place between the electrodes. The electrical resistance between the electrodes in this case falls sharply, and the capacitance is discharged in a damped periodic oscillation. A certain amount of time, called the latency time, passes between the closing of the high-voltage switch and the sharp reduction in the resistance between the electrodes, during which time a small current flows which is essentially limited by the resistance of the liquid medium located between the electrodes.

In order that a voltage breakdown in the form of a spark discharge takes place between the two electrodes, the distance between them must not be less than a certain level, depending on the nature of the liquid medium and magnitude of the intermittently applied voltage. Each spark discharge leads to material being lost at the electrode tips, and thus to a greater electrode separation. As the separation approaches a critical level, then application of the voltage to the electrodes leads to a spark discharge less and less frequently until, finally, such a discharge no longer takes place at all. In addition, the average latency time is increased, with the consequence that some of the stored energy is lost, as a result of the current flowing in this case, even before the voltage breakdown, and correspondingly less energy is available to produce the shock wave.

In the past, there have been a number of attempts to obtain a voltage breakdown even with an electrode separation beyond the critical level, in order on the one hand to increase the life of the devices containing the electrodes and on the other hand to achieve an increase in performance in terms of the shock wave energy, by means of the longer discharge channel.

So-called wire discharge sources are known, in which thin wires are caused to vaporize explosively by a high-current discharge. However, especially in the case of hydraulic lithotripsy, these do not represent a practicable method since the wire has to be replaced after every discharge and a typical lithotripsy treatment involves several thousand discharges.

DE-PS 36 37 326 discloses the use of an auxiliary electrode which leads to a controlled leader geometry and, by virtue of this, to greater electrode separations. The leader is in this case an initially low-current channel which precedes the actual spark discharge and determines its local course. Since very considerable mechanical stresses occur in the vicinity of a spark discharge, a suitable design can be implemented only with difficulty. In addition, the auxiliary electrode has to be supplied with voltage separately from the two main electrodes, so that these devices cannot be used in existing systems.

A different way of obtaining a more efficient shock wave and of lengthening the life of the electrodes is disclosed in DE-PS 40 20 770. The essential feature in this case is that the resistance of the liquid medium between the electrodes is considerably reduced, so that an aperiodic discharge results. The critical resistance required for this purpose is less than about 20 ohm×cm.

The invention is based on the object of achieving a voltage breakdown in the form of a spark discharge between two electrodes located in a liquid medium with an electrode separation that is greater than a critical level, in which case a spark discharge would not take place without further measures with a given liquid medium and a given magnitude of the applied voltage.

The method to achieve the object is specified in claim 1.

The essential feature of the invention is that particles which are conductive, semiconductive or can be polarized are introduced between the electrodes into a liquid medium surrounding said electrodes, and are held there.

These particles do not dissolve. It has been found that, in consequence, a spark discharge takes place even with electrode separations which are considerably greater than the critical level. This contributes to the device containing the electrodes having a considerably longer life. In addition, an improvement in performance is achieved, the efficiency is increased and the usable voltage range is extended. However, no preparatory process is required between the individual discharges, no auxiliary electrodes and voltages are necessary, and it is not necessary to reduce the resistance of the medium between the electrodes in the vicinity of the critical value.

According to a preferred embodiment of the method according to the invention, the particles have sizes from a few micrometers up to several hundred micrometers. Metallic particles, in particular aluminum particles, are preferably used.

Claim 5 relates to the device used to achieve the object. According to this claim, the medium is accommodated, with the particles contained in it, in a sleeve which surrounds the electrodes, and is permeable to shock waves. The sleeve has a filling opening, which can be sealed, and, in addition, at least one opening is provided for the gas produced during the spark discharge to escape from. The diameter of this opening should be of a size to limit the exchange between the sleeve interior and the sleeve exterior of the particles located in the liquid medium. The liquid medium located in the sleeve has the particles added to it once, more than once, or continually.

According to a preferred embodiment of the device according to the invention, at least one electrode is surrounded by an annular shield. This shield absorbs and/or reflects parts of the shock wave produced by the spark discharge. This influences the size and shape of the focus area at the second focus and, particularly if the electrode separations are large, keeps the focus extent at a size which is suitable for the application of extracorporeal shock wave lithotripsy (ESWL).

The shield is preferably made of polyurethane.

The invention will be explained in more detail in the following text with reference to an exemplary embodiment which is illustrated in the drawing, and in which.

Figure 1:
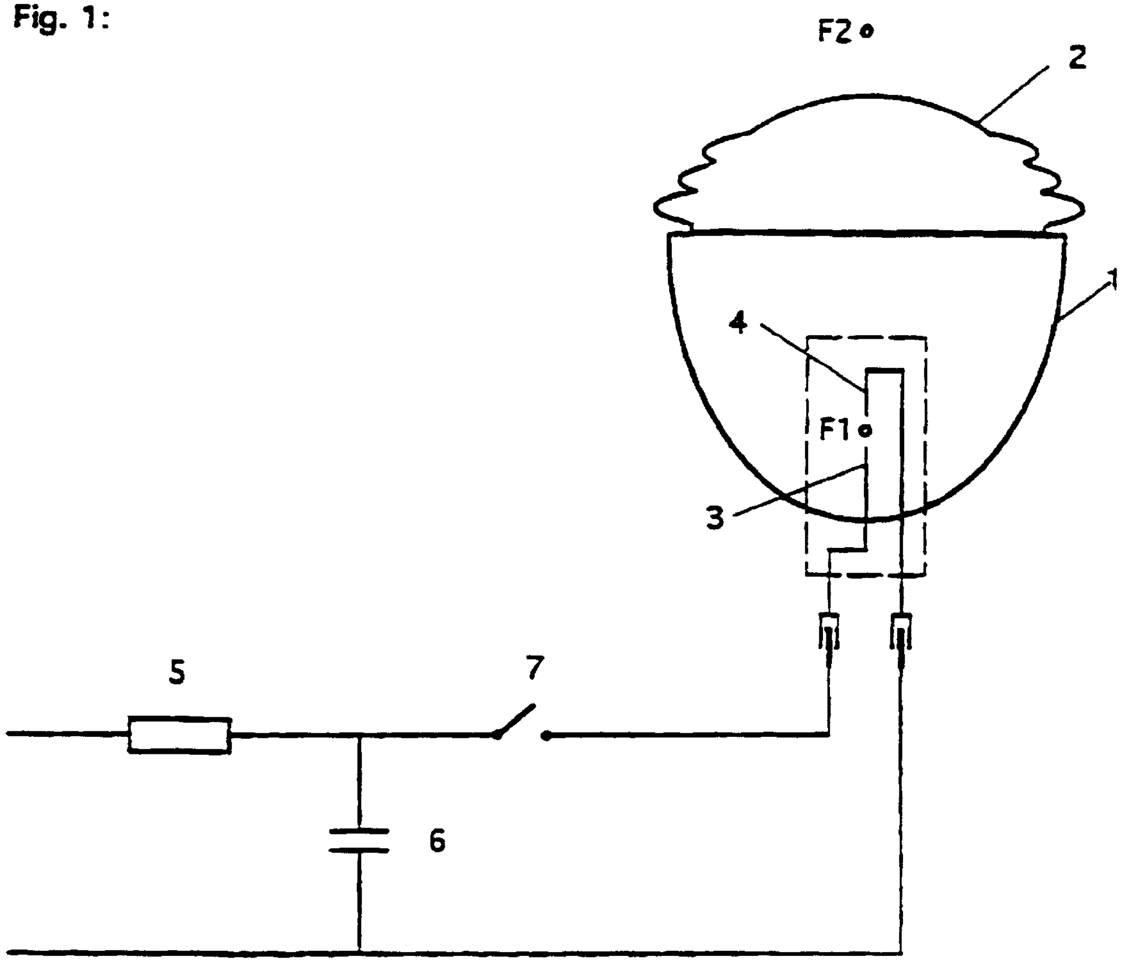
FIG. 1 shows a system for use, in particular, for extracorporeal shock wave lithotripsy (ESWL), using which the method according to the invention is carried out and which includes the device according to the invention.

FIG. 1 shows schematically a section through the longitudinal axis of a truncated rotation ellipsoid. The shock waves coming from a focus F1 are reflected on the wall 1 of the truncated rotation ellipsoid and are focussed toward a focus F2. The truncated rotation ellipsoid is filled with degassed water and is sealed at the top by an elastic membrane 2 which is permeable to shock waves. This membrane 2 is used for acoustic coupling to a body, concretions to be fragmented or tissue to be treated being positioned at the focus F2. There are two opposite electrodes 3 and 4 at the focus F1, on which electrodes the spark discharge takes place, and thus the production of shock waves. The two electrodes 3 and 4 are part of a replaceable device. The electrical circuit has a charging resistance 5, a high-voltage capacitor 6 and a high-voltage switch 7.

Via the charging resistor 5, the high-voltage capacitor 6 is raised, using a high-voltage power source, to a voltage in the order of magnitude of 10,000 V to 30,000 V. The high-voltage capacitor 6 is connected to the two electrodes 3 and 4 via the high-voltage switch 7 which, for example, consists of a triggerable spark gap. If the distance between the two electrodes 3 and 4 is not too great, depending on the magnitude of the voltage applied via the high-voltage switch 7, then a voltage breakdown in the form of a spark discharge takes place between the two electrodes 3 and 4. A discharge channel in the form of a hot plasma is thus formed between the two electrodes 3 and 4, and its rapid expansion leads to a shock wave.

Particles 15 which are conductive, semiconductive or can be polarized and whose size is from a few micrometers to several hundred micrometers are positioned between and/or in the vicinity of the two electrodes 3 and 4, and are held there. It has been found that a spark discharge occurs reliably even if the distances between the electrodes 3 and 4 are greater than a critical level at which voltage breakdown would otherwise no longer take place. The size of the particles is preferably from 50 $\mu$m to 500 $\mu$m.

Figure 2:
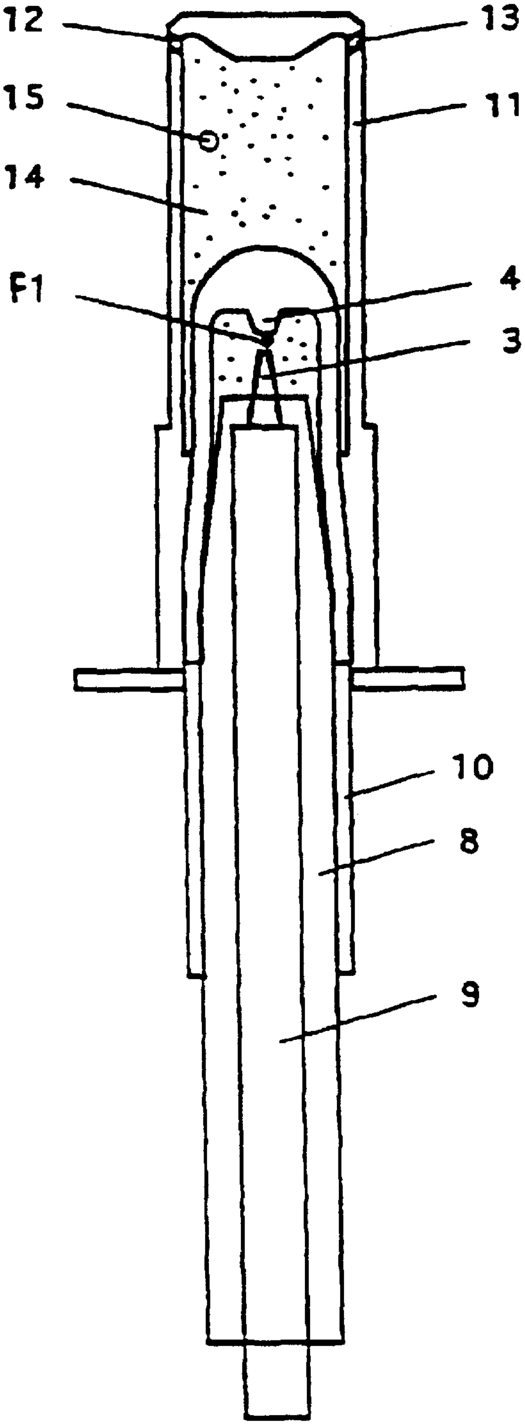
FIG. 2 shows a section illustration of a device including the electrodes.

FIG. 2 shows an exemplary embodiment of a device including the electrodes 3 and 4. The electrode 3 is embedded in plastic insulation 8 and has an electrical supply lead in the form of a metallic inner conductor 9. The electrode 4 is electrically connected to a tubular outer conductor 10. The space around the electrodes 3 and 4 is surrounded by a sleeve 11 which is permeable to shock waves and has two holes 12 and 13, each of several hundred micrometers. The sleeve 11 is filled with degassed water 14, which has a resistivity of about 2000 ohm×cm. The particles 15 are added to the water.

This device is mounted in a system according to FIG. 1 such that the center point between the two electrodes 3 and 4 is located at the focus F1 of the truncated rotation ellipsoid. A high voltage is applied to the electrodes 3 and 4 via the inner conductor 9 and the outer conductor 10, when the high-voltage switch 7 is switched on. After a certain latency time, a spark discharge is then formed between the electrodes 3 and 4, producing a shock wave. During each discharge, material is eroded from the tips of the electrodes 3 and 4, so that the distance between the electrodes becomes increasingly greater. The particles 15 which are conductive, semiconductive or can be polarized result in a spark discharge taking place reliably even if the distance between the electrodes 3 and 4 is considerably greater than a critical level.

The gas which is produced during each spark discharge escapes from the sleeve 11 through the holes 12 and 13. The holes 12 and 13 are in this case introduced such that one of the holes is located at the highest point in the space enclosed by the sleeve 11 in every possible position of the truncated rotation ellipsoid.

Figure 3:
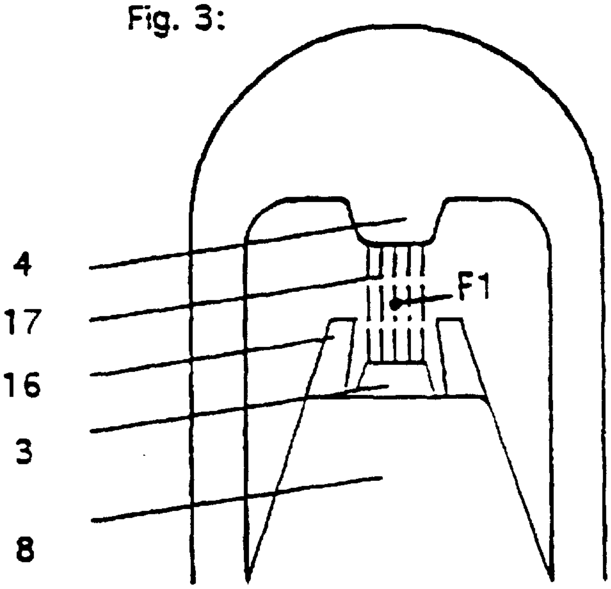
FIG. 3 shows a partial section with a shield for focus limiting.

FIG. 3 shows a sectional illustration of the electrodes 3 and 4, the electrode 3 being surrounded by a rotationally symmetrical shield 16. This shield 16 is made of an electrically non-conductive material which absorbs and/or reflects shock waves. When the electrode separations are large, the shield 16 ensures that shock wave elements which are produced by the discharge channel 17 at a relatively long distance from the focus F1 do not reach the focus F2. The focus area of F2 thus remains small, and corresponds to the area produced by a spark discharge across a short electrode separation.

I claim:

1. Method for producing shock waves by spark discharge between electrodes which are supplied with electrical current intermittent in a liquid medium, the shock waves being focused onto an object located in a body, for medical treatment, in particular for electrohydraulic lithotripsy, the method comprising the steps of:

introducing non-dissolving particles into the liquid medium;

inserting said particles between the electrodes and holding them there to effectively increase the critical electrode separation distance required for spark discharge; and wherein the liquid medium is water.

2. Method according to claim 1, wherein particles having a diameter of from a few micrometers to several hundred micrometers are used.

3. Method according to claim 1, wherein aluminum particles are used.

4. The method of claim 1, wherein said particles are conductive.

5. The method of claim 1, wherein said particles are semiconductive.

6. The method of claim 1, wherein said particles can be polarized.

7. The method of claim 1, further comprising separating said electrodes at a distance greater than the critical level.

8. Device for producing shock waves by spark discharge between electrodes which are supplied with electrical current intermittently in a liquid medium, the shock waves being focused onto an object located in a body, for medical treatment, in particular for electrohydraulic lithotripsy, the device comprising:

non-dissolving particles in the liquid medium between the electrodes; and a sleeve which surrounds the electrodes, wherein the sleeve contains the particles and holds the particles between the electrodes to effectively increase the critical electrode separation distance required for spark discharge, wherein the liquid medium is water, and wherein the sleeve is permeable to shock waves.

9. Device according to claim 8, wherein a shield is arranged at least around one electrode.

10. Device according to claim 9, wherein the shield is made of polyurethane.

11. The device of claim 8, wherein said particles are conductive.

12. The device of claim 8, wherein said particles are semiconductive.

13. The device of claim 8, wherein said particles can be polarized.

14. The device of claim 8, further comprising separating said electrodes at a distance greater than the critical level.

15. The device of claim 8, further comprising at least one opening in the sleeve for gas to escape from.

16. Device for producing shock waves by spark discharge between electrodes which are supplied with electrical current intermittently in a liquid medium, the shock waves being focused onto an object located in a body, for medical treatment, in particular for electrohydraulic lithotripsy, the device comprising:

non-dissolving particles in the liquid medium between the electrodes; and a holder of the particles between the electrodes to effectively increase the critical electrode separation distance required for spark discharge, wherein the liquid medium is water, and wherein the holder is permeable to shock waves.

* * * * *